US012114976B2

(12) United States Patent
Ma et al.

(10) Patent No.: US 12,114,976 B2
(45) Date of Patent: Oct. 15, 2024

(54) INSTRUMENT DELIVERY DEVICES, SYSTEMS, AND METHODS TO EXTEND THROUGH A THROMBUS

(71) Applicant: Becton, Dickinson and Company, Franklin Lakes, NJ (US)

(72) Inventors: Yiping Ma, Layton, UT (US); Jordan Ciciliano, Salt Lake City, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 827 days.

(21) Appl. No.: 17/183,098

(22) Filed: Feb. 23, 2021

(65) Prior Publication Data

US 2021/0275069 A1    Sep. 9, 2021

Related U.S. Application Data

(60) Provisional application No. 62/987,231, filed on Mar. 9, 2020.

(51) Int. Cl.
*A61B 5/15* (2006.01)
*A61M 25/00* (2006.01)
*A61M 25/06* (2006.01)

(52) U.S. Cl.
CPC .......... *A61B 5/150992* (2013.01); *A61B 5/150343* (2013.01); *A61M 25/007* (2013.01); *A61M 25/0606* (2013.01); *A61M 2025/0008* (2013.01)

(58) Field of Classification Search
None
See application file for complete search history.

(56) References Cited

U.S. PATENT DOCUMENTS

| 2012/0277627 A1 | 11/2012 | Devgon |
| 2018/0272107 A1 | 9/2018 | Ehrenreich et al. |
| 2019/0021640 A1 | 1/2019 | Burkholz et al. |

(Continued)

FOREIGN PATENT DOCUMENTS

| WO | 2011/102874 | 8/2011 |
| WO | 2019/018473 | 1/2019 |

OTHER PUBLICATIONS

Velano Vascular, Inc., Pivo Needleless Blood Draw Solution, Webpage, <https://velanovascular.com/solutions/> (last accessed May 19, 2021).

*Primary Examiner* — Yi-Shan Yang
*Assistant Examiner* — Om Patel
(74) *Attorney, Agent, or Firm* — The Webb Law Firm

(57) ABSTRACT

A method may include coupling a first delivery device to a catheter assembly, which may include a catheter dwelling within vasculature of a patient. The first delivery device may include a first tubular instrument. In response to the first tubular instrument being in a distal position, a distal surface of the first tubular instrument may be disposed at a first distance beyond the distal tip of the catheter. The method may include coupling a second delivery device to the catheter assembly after uncoupling the first delivery device from the catheter assembly. The second delivery device may include a second tubular instrument. In response to the second tubular instrument being in the distal position, a distal surface of the second tubular instrument may be disposed at a second distance beyond the distal tip of the catheter. The second distance may be greater than the first distance.

20 Claims, 6 Drawing Sheets

(56) References Cited

U.S. PATENT DOCUMENTS

| | | |
|---|---|---|
| 2019/0321590 A1 | 10/2019 | Burkholz et al. |
| 2019/0321595 A1 | 10/2019 | Spataro et al. |
| 2020/0016374 A1 | 1/2020 | Burkholz et al. |
| 2020/0170559 A1 | 6/2020 | Burkholz et al. |
| 2020/0230353 A1 | 7/2020 | Burkholz et al. |
| 2020/0316346 A1 | 10/2020 | Burkholz et al. |

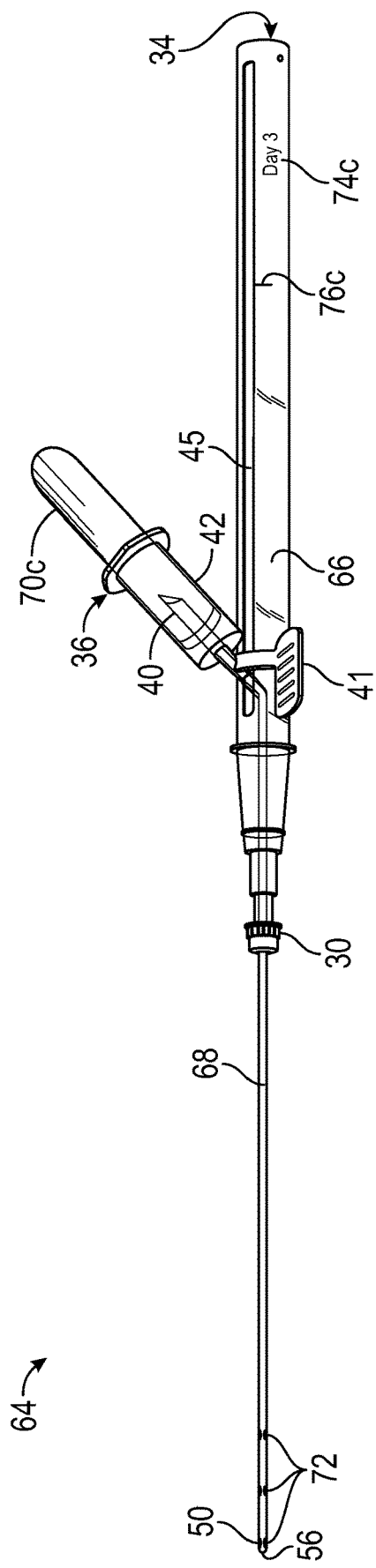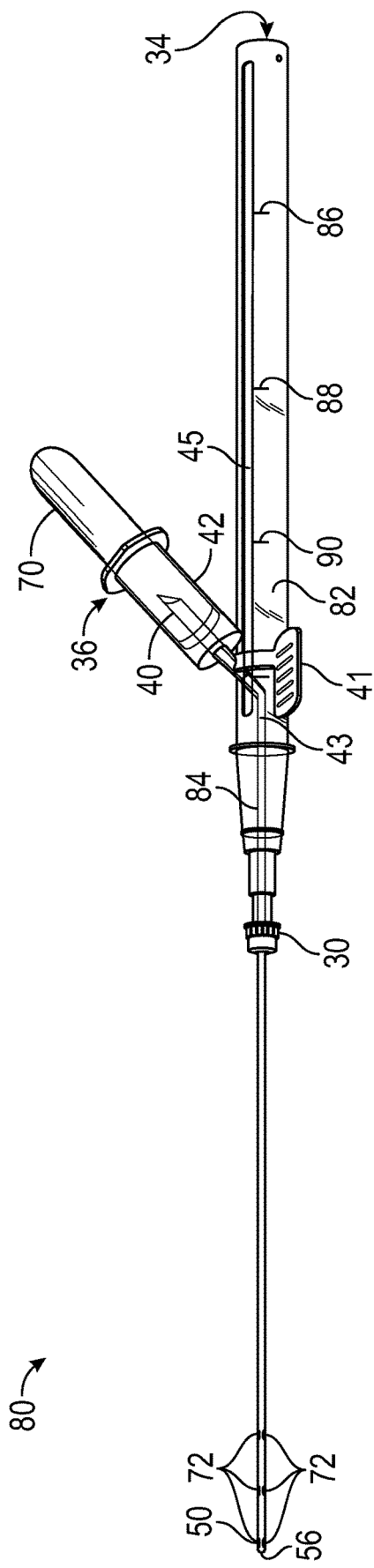

INSTRUMENT DELIVERY DEVICES, SYSTEMS, AND METHODS TO EXTEND THROUGH A THROMBUS

RELATED APPLICATIONS

This application claims the benefit of U.S. Provisional Patent Application No. 62/987,231, filed on Mar. 9, 2020, entitled "INSTRUMENT DELIVERY DEVICES, SYSTEMS, AND METHODS TO EXTEND THROUGH A THROMBUS," which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using the catheter may be difficult for several reasons, particularly when a dwell time of the catheter within the vasculature is more than one day. When the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, the catheter is often used for acquiring a blood sample at a time of catheter placement, but the catheter is less frequently used for acquiring a blood sample during the catheter dwell period. Therefore, when a blood sample is required, an additional needle stick is often needed to provide vein access for blood collection, which may be painful for the patient and result in higher material costs.

In some instances, in order to avoid the additional needle stick, a tubular instrument may be used to access the vasculature of the patient via the catheter. The tubular instrument may be inserted through the catheter and into the vasculature to extend a life of the catheter and allow blood withdrawal through the catheter without the additional needle stick.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to one or more delivery devices that provide access to vasculature of a patient, as well as related systems and methods. In some embodiments, the delivery devices may each deliver a tubular instrument through a catheter. In some embodiments, the tubular instrument may facilitate an increased dwell period of the catheter within the vasculature of the patient. In some embodiments, the delivery devices may be used to advance the tubular instrument into the catheter and/or beyond a distal tip of the catheter when the catheter is compromised or nearing an end of its life to overcome obstructions such as thrombus, valves, and/or a fibrin sheath in or around the catheter that may otherwise prevent blood draw.

In some embodiments, the delivery devices may provide needle-free delivery of the tubular instrument to the vasculature of the patient for blood collection, fluid delivery, patient or device monitoring, or other clinical needs by utilizing an existing catheter dwelling within the vasculature. In some embodiments, the tubular instruments of the delivery devices may be different lengths, and delivery devices with longer tubular instruments may be used after delivery devices with shorter tubular instruments to increase a likelihood of the tubular instruments passing through a thrombus, which may increase in size with time.

In some embodiments, a method may include coupling a first delivery device to a catheter assembly. In some embodiments, the catheter assembly may include a catheter that is dwelling within the vasculature of the patient. In some embodiments, the first delivery device may include a first housing and a first tubular instrument. In some embodiments, the first tubular instrument may include a distal end, a proximal end, and a lumen extending between the distal end of the first tubular instrument and the proximal end of the first tubular instrument. In some embodiments, the proximal end of the first tubular instrument may be secured within the first housing.

In some embodiments, the first tubular instrument may be configured to advance distally from a proximal position to a distal position with respect to the first housing and the catheter assembly. In some embodiments, in response to the first tubular instrument being in the proximal position, the first tubular instrument may be proximal to the catheter assembly. In some embodiments, in response to the first tubular instrument being in the distal position, a distal surface of the distal end of first tubular instrument may be disposed distal to a distal tip of the catheter and at a first distance beyond the distal tip of the catheter. In some embodiments, the first tubular instrument may be fully advanced with respect to the first housing in response to the first tubular instrument being in the distal position.

In some embodiments, after transferring a first volume of blood via the first tubular instrument to a first blood collection container and moving the tubular instrument from the distal position toward the proximal position, the method may include decoupling the first delivery device from the catheter assembly. In some embodiments, after decoupling the first delivery device from the catheter assembly, the method may include coupling a second delivery device to the catheter assembly.

In some embodiments, the second delivery device may include a second housing and a second tubular instrument. In some embodiments, the second tubular instrument may include a distal end, a proximal end, and a lumen extending between the distal end of the second tubular instrument and the proximal end of the second tubular instrument. In some embodiments, the proximal end of the second tubular instrument may be secured within the second housing. In some embodiments, the second tubular instrument may be configured to advance distally from the proximal position to the distal position with respect to the second housing and the catheter assembly. In some embodiments, the second tubular instrument may be fully advanced with respect to the second housing in response to the second tubular instrument being in the distal position.

In some embodiments, in response to the second tubular instrument being in the proximal position, the second tubular instrument may be proximal to the catheter assembly. In some embodiments, in response to the second tubular instrument being in the distal position, a distal surface of the distal end of the second tubular instrument may be disposed distal to the distal tip of the catheter and at a second distance beyond the distal tip of the catheter. In some embodiments, the second distance may be greater than the first distance.

In some embodiments, after transferring a second volume of blood via the second tubular instrument to a second blood collection container and moving the second tubular instrument from the distal position toward the proximal position, the method may include decoupling the second delivery device from the catheter assembly. In some embodiments, after decoupling the second delivery device from the catheter assembly, the method may include coupling a third delivery device to the catheter assembly.

In some embodiments, the third delivery device may include a third housing and a third tubular instrument. In some embodiments, the third tubular instrument may include a distal end, a proximal end, and a lumen extending between the distal end of the third tubular instrument and the proximal end of the third tubular instrument. In some embodiments, the proximal end of the third tubular instrument may be secured within the third housing. In some embodiments, the third tubular instrument may be configured to advance distally from the proximal position to the distal position with respect to the third housing and the catheter assembly. In some embodiments, the third tubular instrument may be fully advanced with respect to the third housing in response to the third tubular instrument being in the distal position.

In some embodiments, in response to the third tubular instrument being in the proximal position, the third tubular instrument may be proximal to the catheter assembly. In some embodiments, in response to the third tubular instrument being in the distal position, a distal surface of the distal end of the third tubular instrument may be disposed distal to the distal tip of the catheter and at a third distance beyond the distal tip of the catheter. In some embodiments, the third distance may be greater than the second distance. In some embodiments, after transferring a third volume of blood via the third tubular instrument to a third blood collection container and moving the third tubular instrument from the distal position toward the proximal position, the method may include decoupling the third delivery device from the catheter assembly.

In some embodiments, a difference between the first distance and the second distance may be 0.5 inches, which may facilitate extension through the thrombus that may be formed near the distal tip of the catheter and establishment of a fluid pathway through the catheter assembly. In further detail, in some embodiments, a size of the thrombus may increase over time, so the second distance may be greater than the first distance to increase a likelihood of passing through the thrombus when the second delivery device is coupled to the catheter assembly, which after the first delivery device is coupled to the catheter assembly. In some embodiments, the first distance may be 1 inch or less. In some embodiments, the second distance may be 1.5 inches or less. In some embodiments, the third distance may be 2 inches or less.

In some embodiments, a difference between the first distance and the second distance may be 0.25 inches, 0.33 inches, 0.75 inches, 1 inch, or another suitable distance. In some embodiments, a difference between the first distance and the second distance may be greater than 0.25 inches. In some embodiments, the first delivery device may be coupled to the catheter assembly on a first day, and the second delivery device may be coupled to the catheter assembly on a second day, which may be subsequent to the first day. In some embodiments, the second day may immediately follow the first day.

In some embodiments, a difference between the second distance and the third distance may be 0.5 inches, which facilitate extension through the thrombus that may be formed near the distal tip of the catheter and establishment of the fluid pathway through the catheter assembly. In further detail, in some embodiments, the size of the thrombus may increase over time, so the third distance may be greater than the second distance to increase a likelihood of passing through the thrombus when the third delivery device is coupled to the catheter assembly, which may occur after the second delivery device is coupled to the catheter assembly.

In some embodiments, a difference between the second distance and the third distance may be 0.25 inches, 0.33 inches, 0.75 inches, 1 inch, or another suitable distance. In some embodiments, a difference between the second distance and the third distance may be greater than 0.25 inches. In some embodiments, the second delivery device may be coupled to the catheter assembly on the second day, and the third delivery device may be coupled to the catheter assembly on the third day, which may be subsequent to the second day. In some embodiments, the third day may immediately follow the second day.

In some embodiments, the first volume of blood may be transferred to the first blood collection container via the first tubular instrument on the first day. In some embodiments, the second volume of blood may be transferred to the second blood collection container via the second tubular instrument on the second day. In some embodiments, the third volume of blood may be transferred to the third blood collection container via the third tubular instrument on the third day. In some embodiments, one or more of the first volume of blood, the second volume of blood, and the third volume of blood may be equal to each other or different from each other.

In some embodiments, a distal end of one or more of the first tubular instrument, the second tubular instrument, and the third tubular instrument may include one or more side holes, which may facilitate blood flow into the catheter proximal to the thrombus. In some embodiments, the distal end of one or more of the first tubular instrument, the second tubular instrument, and the third tubular instrument may be closed and/or may include a slit. In some embodiments, one or more of the first tubular instrument, the second tubular instrument, and the third tubular instrument may be resistant to occlusion and thrombosis because the slit may be closed and blood may not be allowed to diffuse into the corresponding tubular instrument under normal physiological pressures.

In some embodiments, the difference between the first distance and the second distance and the difference between the second distance and the third distance may increase a likelihood of extension through the thrombus and establishment of the fluid pathway through the catheter assembly. In some embodiments, one or more particular delivery devices in addition to the first delivery device, the second delivery device, and the third delivery device may be coupled to the catheter assembly without removing the catheter from the patient. In some embodiments, particular tubular instruments that are inserted through the dwelling catheter as time progresses may be increasingly longer, which may increase a likelihood of establishing the fluid pathway through the catheter assembly to allow blood draw and/or may reduce thrombosis.

In some embodiments, the first delivery device may include a first marking. In some embodiments, the second delivery device may include a second marking. In some embodiments, the third delivery device may include a third marking. In some embodiments, one or more of the first marking, the second marking, and the third marking may include a time to use the corresponding delivery device. For example, the first marking may include "Day 1" or "First Blood Draw." As another example, the second marking may include "Day 2" or "Second Blood Draw." As a further example, the third marking may include "Day 3" or "Third Blood Draw." In some embodiments, the first marking, the second marking, and/or the third marking may indicate a time to use the corresponding delivery devices with respect to each other.

In some embodiments, the first delivery device may include another marking. In some embodiments, the first delivery device may include a slider, which may be coupled to the first tubular instrument. In some embodiments, the slider may be aligned with the other marking in response to the distal surface of the first tubular instrument being flush with the distal tip of the catheter. Thus, in some embodiments, the other marking may indicate to a clinician that in response to further advancement of first tubular instrument in a distal direction, the first tubular instrument will extend distal to the distal tip.

In some embodiments, the second delivery device may include the other marking. In some embodiments, the second delivery device may include the slider that may be coupled to the second tubular instrument. In some embodiments, the slider may be aligned with the other marking in response to the distal surface of the second tubular instrument being flush with the distal tip of the catheter. Similarly, in some embodiments, the third delivery device may include the other marking. In some embodiments, the third delivery device may include the slider, which may be coupled to the third tubular instrument. In some embodiments, the slider may be aligned with the other marking in response to the distal surface of the third tubular instrument being flush with the distal tip of the catheter.

In some embodiments, the catheter assembly may include a catheter adapter, which may include a distal end, a proximal end, and a lumen extending through the distal end of the catheter adapter and the proximal end of the catheter adapter. In some embodiments, the catheter assembly may include the catheter, which may be secured within the catheter adapter. In some embodiments, a distal end of the housing may include a connector, which may be configured to couple to a connector of the catheter adapter.

In some embodiments, another delivery device may include the housing, which may include one or more of the following: the first marking, the second marking, the third marking, and a slot. In some embodiments, the first marking is proximal to the second marking. In some embodiments, the delivery device may include a tubular instrument, which may include a distal end, a proximal end, and a lumen extending between the distal end of the tubular instrument and the proximal end of the tubular instrument. In some embodiments, the proximal end of the tubular instrument may be secured within the housing. In some embodiments, the slider may be coupled to the tubular instrument and slidable along the slot of the housing. In some embodiments, the slider may include an advancement tab, which may be gripped by the clinician to advance and/or retract the tubular instrument.

In some embodiments, in response to advancing the slider distally from a proximal position to the first marking, a distal surface of the distal end of the tubular instrument may be disposed at a first distance beyond the distal end of the housing. In some embodiments, in response to advancing the slider distally from the proximal position to the second marking, the distal surface of the distal end of the tubular instrument may be disposed at a second distance beyond the distal end of the housing. In some embodiments, the second distance beyond the distal end of the housing may be greater than the first distance beyond the distal end of the housing. In some embodiments, in response to advancing the slider distally from the proximal position to the third marking, the distal surface of the distal end of the tubular instrument may be disposed at a third distance beyond the distal end of the housing. In some embodiments, the third distance beyond the distal end of the housing may be greater than the second distance beyond the distal end of the housing.

It is to be understood that both the foregoing general description and the following detailed description are examples and explanatory and are not restrictive of the invention, as claimed. It should be understood that the various embodiments are not limited to the arrangements and tubular instrumentality shown in the drawings. Also, the drawings are not necessarily to scale. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 3C is an upper perspective view of the third delivery device of FIG. 2C, illustrating the third tubular instrument in a distal position, according to some embodiments; and FIG. 4 is an upper perspective view of an elongated delivery device, according to some embodiments.

DESCRIPTION OF EMBODIMENTS

Figure 1A:
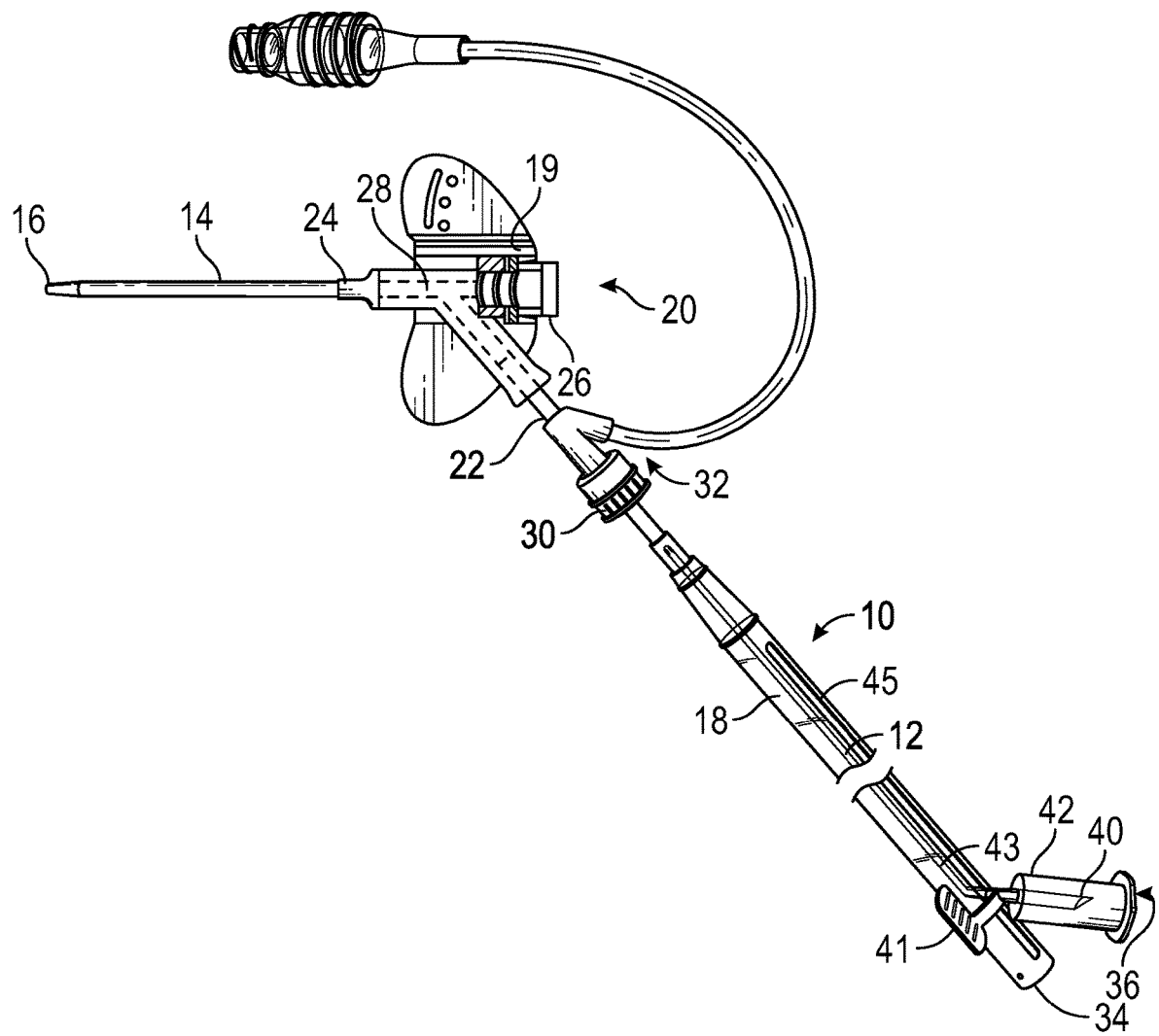
FIG. 1A is an upper perspective view of an example delivery device coupled with an example catheter assembly, illustrating an example tubular instrument in a proximal position, according to some embodiments.
Figure 1B:
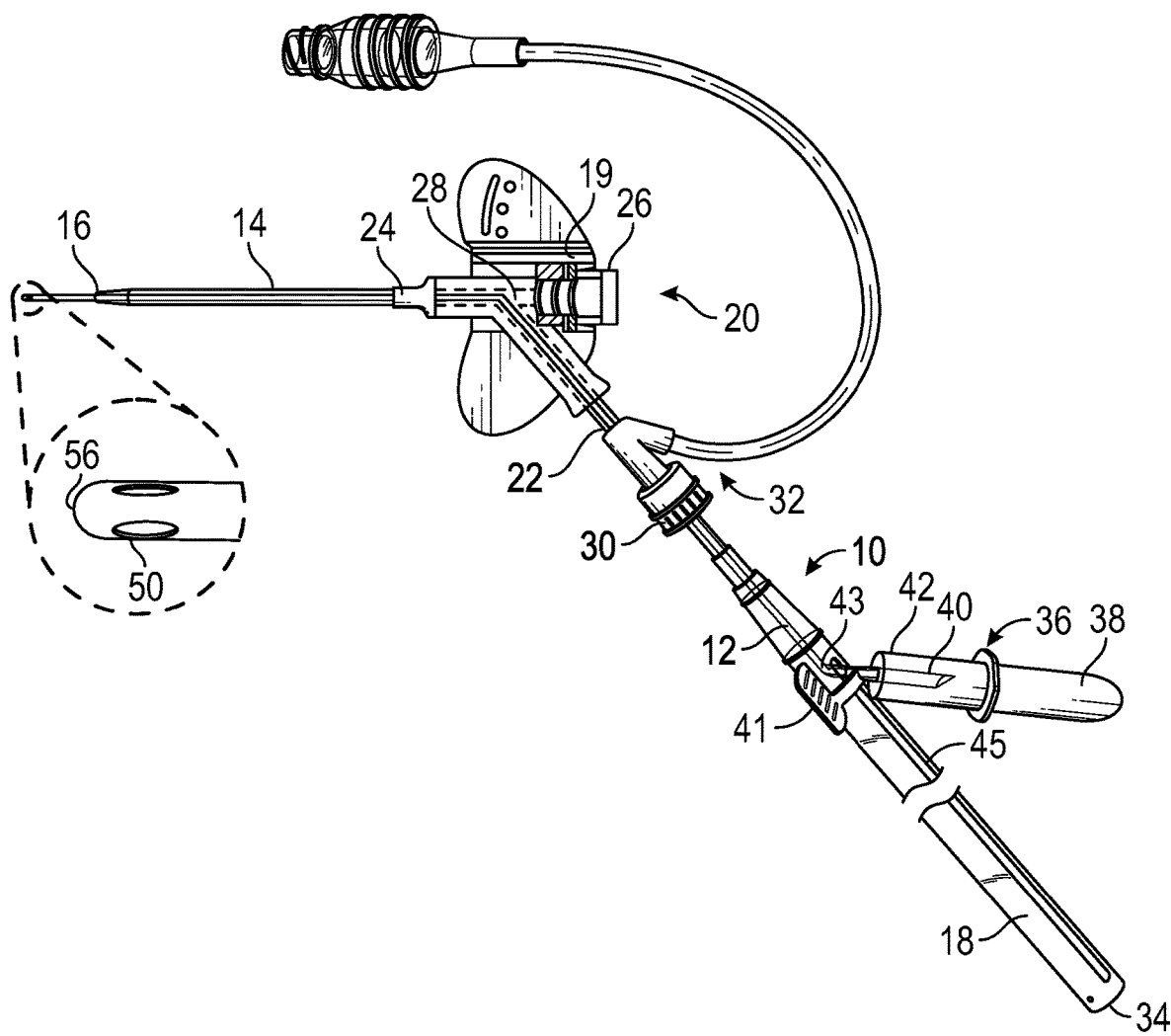
FIG. 1B is an upper perspective view of the delivery device of FIG. 1A coupled with the catheter assembly, illustrating the tubular instrument in a distal position, according to some embodiments.

Referring now to FIGS. 1A-1B, in some embodiments, a delivery device 10 to deliver a tubular instrument 12 into the catheter 14 may facilitate an increased dwell period of the catheter 14. In further detail, the delivery device 10 may be used to advance the tubular instrument 12 into the catheter 14 and/or beyond a distal tip 16 of the catheter 14 for fluid infusion or blood draw when the catheter 14 is compromised or nearing an end of its life.

In some embodiments, the delivery device 10 may include a housing 18 configured to couple to a catheter adapter 19. In some embodiments, the delivery device 10 may include the tubular instrument 12. In some embodiments, the delivery device 10 may include any suitable delivery device. Non-limiting examples of delivery devices that may be used with the tubular instrument 12 are described further in in U.S. patent application Ser. No. 16/037,246, filed Jul. 17, 2018, entitled "EXTENSION HOUSING A PROBE OR INTRAVENOUS CATHETER," U.S. patent application Ser. No. 16/388,650, filed Apr. 18, 2019, entitled "INSTRUMENT DELIVERY DEVICE HAVING A ROTARY ELEMENT," U.S. patent application Ser. No. 16/037,319, filed Jul. 17, 2018, entitled "MULTI-DIAMETER CATHETER AND RELATED DEVICES AND METHODS," U.S. patent application Ser. No. 16/502,541, filed Jul. 3, 2019, entitled "DELIVERY DEVICE FOR A VASCULAR ACCESS INSTRUMENT," U.S. patent application Ser. No. 16/691,217, filed Nov. 21, 2019, entitled "SYRINGE-BASED DELIVERY DEVICE FOR A VASCULAR ACCESS INSTRUMENT," U.S. patent application Ser. No. 16/742,013, filed Jan. 14, 2020, entitled "CATHETER DELIVERY DEVICE AND RELATED SYSTEMS AND METHODS," and U.S. patent application Ser. No. 16/838,831, filed Apr. 2, 2020, entitled "VASCULAR ACCESS INSTRUMENT HAVING A FLUID PERMEABLE STRUCTURE AND RELATED DEVICES AND METHODS," which are each incorporated by reference in their entirety.

In some embodiments, in response to the tubular instrument 12 being advanced distally with respect to the housing 18, the delivery device 10 may be configured to introduce the tubular instrument 12 into the catheter assembly 20, which may include the catheter adapter 19 and the catheter 14. In some embodiments, in response to the tubular instrument 12 being introduced into the catheter assembly 20, the tubular instrument 12 may access a fluid pathway of the catheter assembly 20 and/or the tubular instrument 12 may extend through the catheter assembly 20 to access the vasculature of the patient.

In some embodiments, the catheter assembly 20 may include or correspond to any suitable catheter assembly, such as, for example, the BD NEXIVA™ Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable catheter assembly. In some embodiments, the catheter assembly 20 may be integrated with an integrated extension tube 22. In other embodiments, the catheter assembly 20 may be non-integrated. In some embodiments, the catheter 14 may include a peripheral intravenous catheter (PIVC), a peripherally inserted central catheter (PICC), or a midline catheter.

In some embodiments, the catheter 14 may be secured within and extend distally from the catheter adapter 19. In some embodiments, the catheter adapter 19 may include a distal end 24, a proximal end 26, and a lumen 28 extending between and/or through the distal end 24 and the proximal end 26. In some embodiments, a septum may be disposed within the lumen of the catheter adapter 19. In some embodiments, the tubular instrument 12 may be delivered to the vasculature through the septum or proximal to the septum.

In some embodiments, the delivery device 10 may include a connector 30, which may be coupled to the proximal end 26 or another portion of the catheter assembly 20, such as, for example, a Y-adapter. In some embodiments, the connector 30 may include a slip or thread or clip male luer adapter. In some embodiments, the connector 30 may include a slip or thread or clip female luer adapter. In some embodiments, the connector 30 may include an introducer or cannula that may be inserted into the proximal end 26 of the catheter adapter 19. In some embodiments, the housing 18 may include a distal end 32 and a proximal end 34. In some embodiments, the distal end 32 may include the connector 30.

In some embodiments, the delivery device 10 may include a blood collection device 36. In some embodiments, the blood collection device 36 may include or correspond to a blood collection container. In some embodiments, the blood collection container may include a syringe, an evacuated blood collection tube 38, a small sample collection device, or any other container. In some embodiments, the blood collection device 36 may be coupled to the delivery device 10 after advancement of the tubular instrument 12 in the distal direction.

In some embodiments, the blood collection device may include a needle assembly, which may include a needle 40 configured to receive the blood collection container. In some embodiments, a proximal tip of the needle 40 may be disposed within an elastomeric sheath. In some embodiments, in response to the blood collection container pushing the elastomeric sheath distally, the needle 40 may pierce the elastomeric sheath and be inserted into the blood collection container. In these and other embodiments, the blood collection container may include the evacuated blood collection tube 38.

In some embodiments, the blood collection device may include a holder 42, which may be configured to receive the evacuated blood collection tube 38. In some embodiments, the blood collection device may include the VACUTAINER© one-use holder, available from Becton, Dickinson and Company of Franklin Lakes, New Jersey. In some embodiments, the blood collection device 36 may be coupled to and in fluid communication with the proximal end 43 of the tubular instrument 12. In some embodiments, the blood collection device 36 may be coupled to and in fluid communication with the proximal end 43 of the tubular instrument 12 via a fluid pathway extending through the needle 40 and the tubular instrument 12. In some embodiments, the blood collection device 36 may be coupled to a proximal end 43 of the tubular instrument 12 in any number of suitable ways, such as via integration, a luer connection, etc.

In some embodiments, the delivery device 10 may include an advancement element. In some embodiments, the advancement element may include a tab or a grip, which may be moved by the clinician to advance the tubular instrument 12 in a distal direction and/or retract the tubular instrument 12 in a proximal direction. In some embodiments, the advancement element may be coupled to the tubular instrument 12. In some embodiments, the advancement element may be rotated. In some embodiments, the advancement element may include a slider 41, which may be slidable along a slot 45 disposed within the housing 18, as illustrated in FIGS. 1A-1B. In some embodiments, the tubular instrument 12 may extend and move through the proximal end 26 of the housing 18.

In some embodiments, in response to significant dwelling time within the vasculature, the catheter 14 of the catheter assembly 20 may be susceptible to narrowing, collapse, kinking, blockage by debris (e.g., fibrin or platelet clots), and adhering of the distal tip 16 of the catheter 14 to the vasculature. Thus, blood withdrawal using the catheter 14 may be difficult. In some embodiments, the tubular instrument 12 may include or act as another catheter that may provide access to the vasculature of the patient without any additional needle sticks without any additional needle sticks. Thus, in some embodiments, the tubular instrument 12 may be used for needle-free blood collection and/or fluid infusion.

Figure 2A:
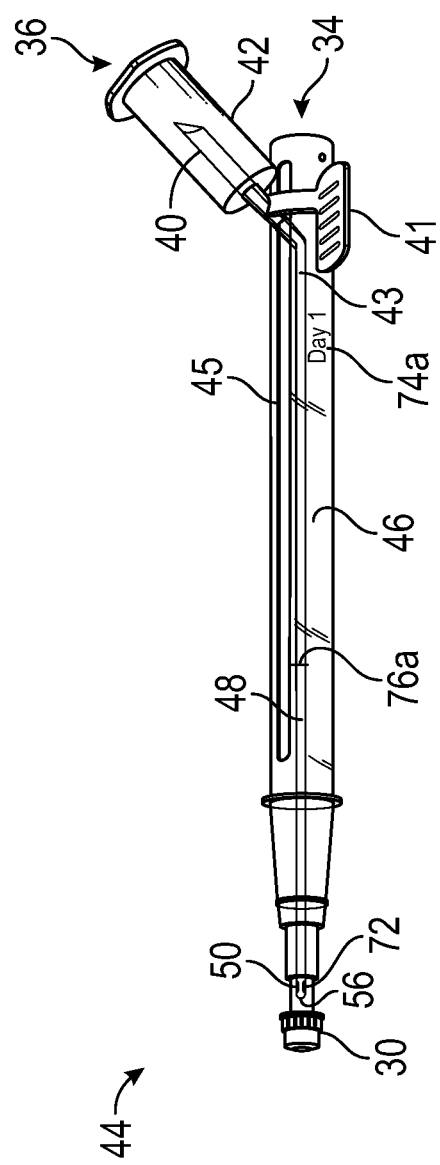
FIG. 2A is an upper perspective view of a first delivery device, illustrating an example first tubular instrument in a proximal position, according to some embodiments.
Figure 3A:
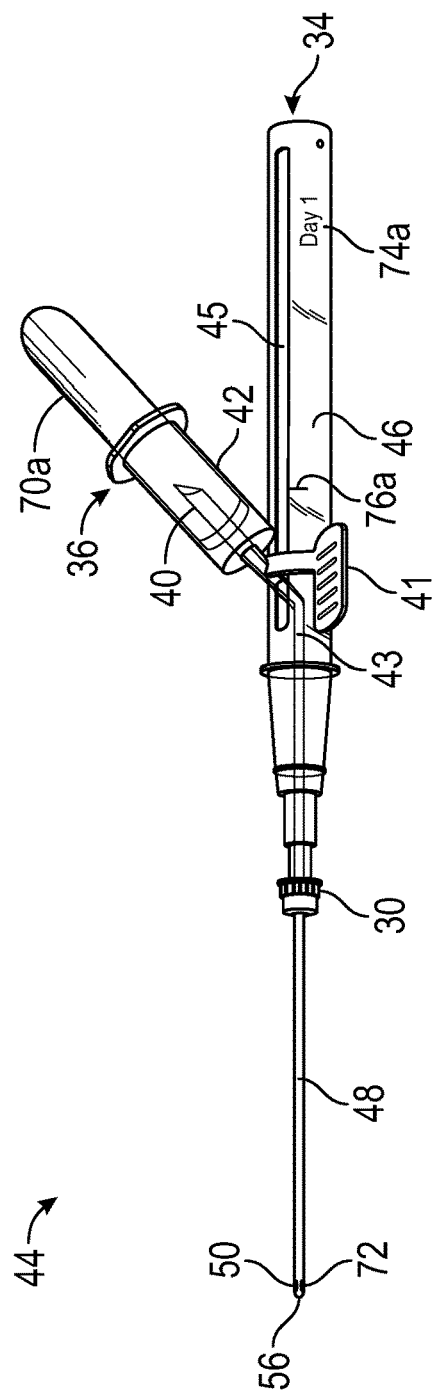
FIG. 3A is an upper perspective view of the first delivery device of FIG. 2A, illustrating the first tubular instrument in a distal position, according to some embodiments.

Referring now to FIGS. 2A and 3A, in some embodiments, a first delivery device 44 may be coupled to the catheter assembly 20. In some embodiments, the first delivery device 44 may be similar or identical to the delivery device 10 of FIGS. 1A-1B, respectively, in terms of one or more included features and/or operation. In some embodiments, the catheter 14 may be dwelling within the vasculature of the patient when the first delivery device 44 is coupled to the catheter assembly 20. In further detail, the catheter 14 may be dwelling within the vasculature of the patient prior to coupling of the first delivery device 44 to the catheter assembly 20.

In some embodiments, the first delivery device 44 may include a first housing 46 and a first tubular instrument 48. In some embodiments, the first housing 46 and the first tubular instrument 48 may be similar or identical to the housing 18 and the tubular instrument 12 of FIGS. 1A-1B in terms of one or more included features and/or operation. In some embodiments, the first tubular instrument 48 may include a distal end 50, the proximal end 43, and a lumen extending between the distal end 50 of the first tubular instrument 48 and the proximal end 43 of the first tubular instrument 48. In some embodiments, the lumen may extend through the distal end 50 and the proximal end 43. In some embodiments, the proximal end 43 of the first tubular instrument 48 may be secured within the first housing 46.

In some embodiments, the first tubular instrument 48 may be configured to advance distally from a proximal position to a distal position with respect to the first housing 46 and the catheter assembly 20. In some embodiments, in response to the first tubular instrument 48 being in the proximal position, the first tubular instrument 48 may be proximal to the catheter assembly 20. In further detail, the distal end 50 of the first tubular instrument 48 or a distal surface 56 of the first tubular instrument 48 may be proximal to the catheter assembly 20 and/or within the first housing 46.

In some embodiments, in response to the first tubular instrument 48 being in the distal position, the distal surface 56 of the distal end 50 of first tubular instrument 48 may be disposed distal to a distal tip 16 of the catheter 14 and at a first distance beyond the distal tip 16 of the catheter 14. In some embodiments, the distal surface 56 may include a distal-most surface of the distal end 50. In some embodiments, the first tubular instrument 48 may be fully advanced with respect to the first housing 46 in response to the first tubular instrument 48 being in the distal position. For example, the slider 41 may contact a distal end of the slot 45, which may act as a stop.

In some embodiments, after transferring a first volume of blood via the first tubular instrument 48 to a first blood collection container and moving the first tubular instrument 48 from the distal position toward the proximal position, the first delivery device 44 may be decoupled from the catheter assembly 20.

Figure 2B:
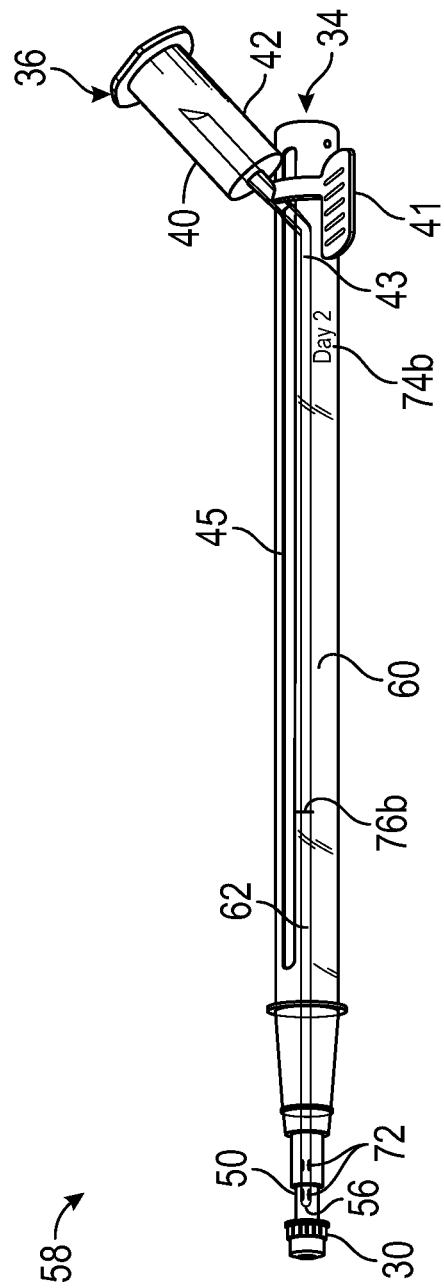
FIG. 2B is an upper perspective view of a second delivery device, illustrating an example second tubular instrument in a proximal position, according to some embodiments.
Figure 3B:
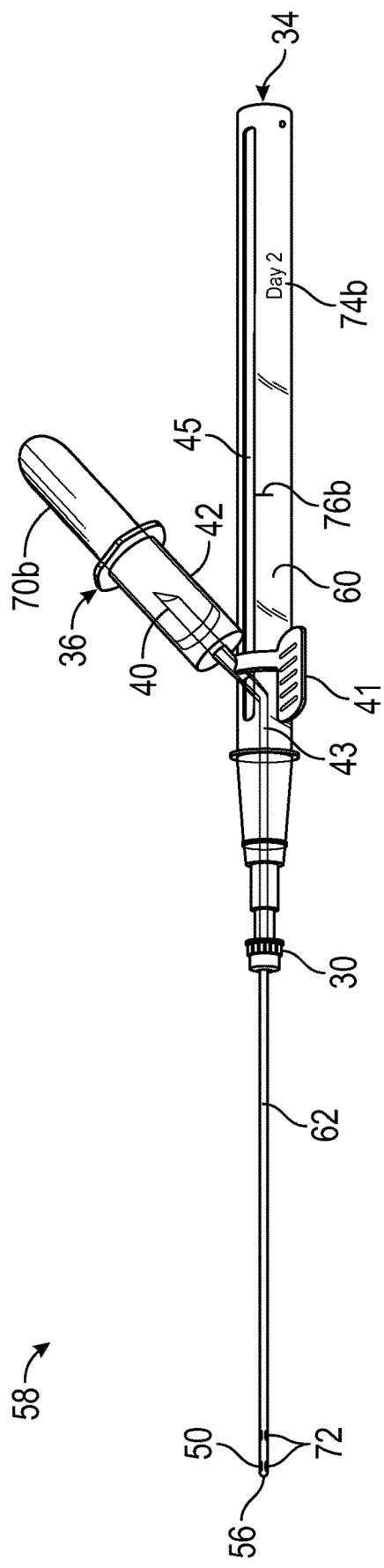
FIG. 3B is an upper perspective view of the second delivery device of FIG. 2B, illustrating the second tubular instrument in a distal position, according to some embodiments.

Referring now to FIGS. 2B and 3B, in some embodiments, after decoupling the first delivery device 44 from the catheter assembly 20, a second delivery device 58 may be coupled to the catheter assembly 20. In some embodiments, the second delivery device 58 may be similar or identical to the delivery device 10 of FIGS. 1A-1B in terms of one or more included features and/or operation. In some embodiments, the catheter 14 may be dwelling within the vasculature of the patient when the second delivery device 58 is coupled to the catheter assembly 20 and may not have been removed from the patient since insertion into the vasculature. In some embodiments, the catheter 14 may be dwelling within the vasculature of the patient prior to coupling of the second delivery device 58 to the catheter assembly 20.

In some embodiments, the second delivery device 58 may include a second housing 60 and a second tubular instrument 62. In some embodiments, the second housing 60 and the second tubular instrument 62 may be similar or identical to the housing 18 and the tubular instrument 12 of FIGS. 1A-1B, respectively, in terms of one or more included features and/or operation. In some embodiments, the second tubular instrument 62 may include the distal end 50, the proximal end 43, and the lumen extending between the distal end 50 of the second tubular instrument 62 and the proximal end 43 of the second tubular instrument 62. In some embodiments, the lumen may extend through the distal end 50 and the proximal end 43.

In some embodiments, the proximal end 43 of the second tubular instrument 62 may be secured within the second housing 60. In some embodiments, the second tubular instrument 62 may be configured to advance distally from the proximal position to the distal position with respect to the second housing 60 and the catheter assembly 20. In some embodiments, the second tubular instrument 62 may be fully advanced with respect to the second housing 60 in response to the second tubular instrument 62 being in the distal position. For example, the slider 41 may contact a distal end of the slot 45, which may act as a stop.

In some embodiments, in response to the second tubular instrument 62 being in the proximal position, the second tubular instrument 62 may be proximal to the catheter assembly 20. In further detail, the distal end 50 of the second tubular instrument 62 or the distal surface 56 of the second tubular instrument 62 may be proximal to the catheter assembly 20 and/or within the second housing 60. In some embodiments, in response to the second tubular instrument 62 being in the distal position, the distal surface 56 of the distal end 50 of the second tubular instrument 62 may be disposed distal to the distal tip 16 of the catheter 14 and at a second distance beyond the distal tip 16 of the catheter 14. In some embodiments, the distal surface 56 may include a distal-most surface of the distal end 50. In some embodiments, the second distance may be greater than the first distance.

In some embodiments, after transferring a second volume of blood via the second tubular instrument 62 to a second blood collection container and moving the second tubular instrument 62 from the distal position toward the proximal position, the second delivery device 58 may be decoupled from the catheter assembly 20.

In some embodiments, a difference between the first distance and the second distance may be 0.5 inches, which may facilitate extension through a thrombus that may be formed near the distal tip 16 of the catheter 14 and establishment of a fluid pathway through the catheter assembly 20. In further detail, in some embodiments, a size of the thrombus may increase over time, so the second distance may be greater than the first distance to increase a likelihood of the second tubular instrument 62 passing through the thrombus when the second delivery device is coupled to the catheter assembly 20, which after the first delivery device is coupled to the catheter assembly 20. In some embodiments, the first distance may be 1 inch or less. In some embodiments, the second distance may be 1.5 inches or less.

In some embodiments, a difference between the first distance and the second distance may be 0.25 inches, 0.33 inches, 0.75 inches, 1 inch, or another suitable distance. In some embodiments, a difference between the first distance and the second distance may be greater than 0.25 inches. In some embodiments, the first delivery device may be coupled to the catheter assembly 20 on a first day, and the second delivery device may be coupled to the catheter assembly 20 on a second day, which may be subsequent to the first day. In some embodiments, the second day may immediately follow the first day.

Figure 2C:
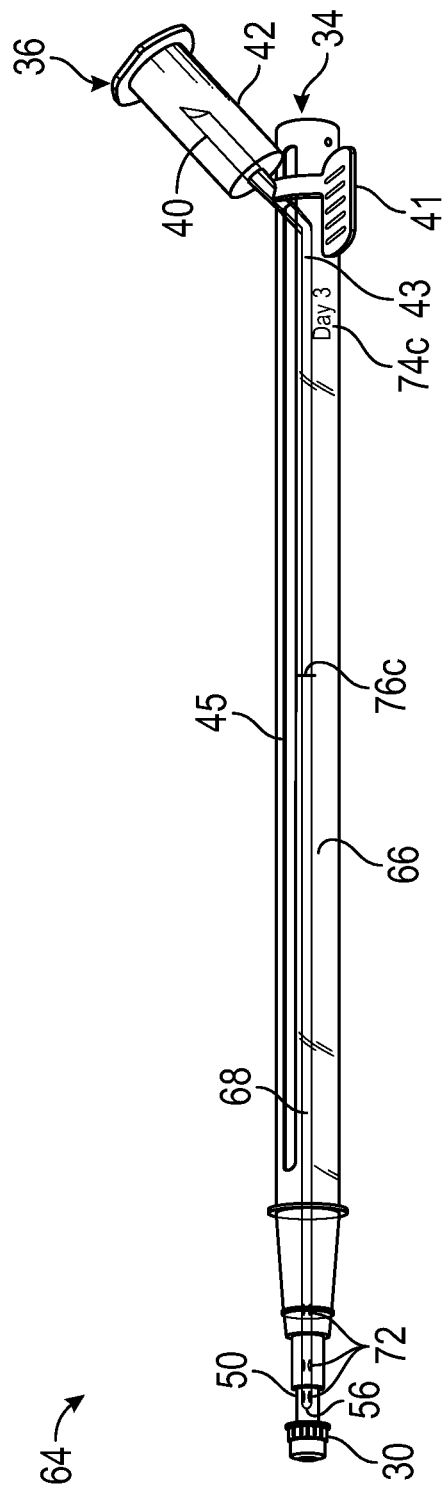
FIG. 2C is an upper perspective view of a third delivery device, illustrating an example third tubular instrument in a proximal position, according to some embodiments.

Referring now to FIGS. 2C and 3C, in some embodiments, after decoupling the second delivery device 58 from the catheter assembly 20, a third delivery device 64 may be coupled to the catheter assembly 20. In some embodiments, the third delivery device 64 may be similar or identical to the delivery device 10 of FIGS. 1A-1B in terms of one or more included features and/or operation. In some embodiments, the catheter 14 may be dwelling within the vasculature of the patient when the third delivery device 64 is coupled to the catheter assembly 20 and may not have been removed from the patient since insertion into the vasculature. In some embodiments, the catheter 14 may be dwelling within the vasculature of the patient prior to coupling of the second delivery device 58 to the catheter assembly 20.

In some embodiments, the third delivery device 64 may include a third housing 66 and a third tubular instrument 68. In some embodiments, the third housing 66 and the third tubular instrument 68 may be similar or identical to the housing 18 and the tubular instrument 12 of FIGS. 1A-1B, respectively, in terms of one or more included features and/or operation. In some embodiments, the third tubular instrument 68 may include the distal end 50, the proximal end 43, and the lumen extending between the distal end 50 and the proximal end 43. In some embodiments, the lumen may extend through the distal end 50 and the proximal end 43.

In some embodiments, the proximal end 43 of the third tubular instrument 68 may be secured within the third housing 66. In some embodiments, the third tubular instrument 68 may be configured to advance distally from the proximal position to the distal position with respect to the third housing 66 and the catheter assembly 20. In some embodiments, the third tubular instrument 68 may be fully advanced with respect to the third housing 66 in response to the third tubular instrument 68 being in the distal position. For example, the slider 41 may contact a distal end of the slot 45, which may act as a stop.

In some embodiments, in response to the third tubular instrument 68 being in the proximal position, the third tubular instrument 68 may be proximal to the catheter assembly 20. In further detail, the distal end 50 of the third tubular instrument 68 or the distal surface 56 of the third tubular instrument 68 may be proximal to the catheter assembly 20 and/or within the third housing 66. In some embodiments, in response to the third tubular instrument 68 being in the distal position, the distal surface 56 of the distal end of the third tubular instrument 68 may be disposed distal to the distal tip 16 of the catheter 14 and at a third distance beyond the distal tip 16 of the catheter 14. In some embodiments, the distal surface 56 may include a distal-most surface of the distal end 50. In some embodiments, the third distance may be greater than the second distance.

In some embodiments, after transferring a third volume of blood via the third tubular instrument 68 to a third blood collection container and moving the third tubular instrument 68 from the distal position toward the proximal position, the third delivery device 64 may be decoupled from the catheter assembly 20.

In some embodiments, the third distance may be 2 inches or less. In some embodiments, a difference between the second distance and the third distance may be 0.5 inches, which facilitate extension through the thrombus that may be formed near the distal tip of the catheter and establishment of the fluid pathway through the catheter assembly 20. In further detail, in some embodiments, the size of the thrombus may increase over time, so the third distance may be greater than the second distance to increase a likelihood of the third tubular instrument 68 passing through the thrombus when the third delivery device is coupled to the catheter assembly 20, which may occur after the second delivery device is coupled to the catheter assembly 20.

In some embodiments, a difference between the second distance and the third distance may be 0.25 inches, 0.33 inches, 0.75 inches, 1 inch, or another suitable distance. In some embodiments, a difference between the second distance and the third distance may be greater than 0.25 inches. In some embodiments, the second delivery device 58 may be coupled to the catheter assembly 20 on the second day, and the third delivery device 64 may be coupled to the catheter assembly 20 on the third day, which may be subsequent to the second day. In some embodiments, the third day may immediately follow the second day.

Referring now to FIGS. 2A-3C, in some embodiments, the first volume of blood may be transferred to the first blood collection container 70a via the first tubular instrument 48 on the first day. In some embodiments, the second volume of blood may be transferred to the second blood collection container 70b via the second tubular instrument 62 on the second day. In some embodiments, the third volume of blood may be transferred to the third blood collection container 70c via the third tubular instrument 68 on the third day.

In some embodiments, one or more of the first volume of blood, the second volume of blood, and the third volume of blood may be equal to each other or different from each other. In some embodiments, one or more of the first blood collection container 70a, the second blood collection container 70b, and the third blood collection container 70c may be a same blood collection container or different blood collection containers. In some embodiments, the first volume of blood may be collected in the first blood collection container 70a and/or one or more other blood collection containers. In some embodiments, the second volume of blood may be collected in the second blood collection container 70b and/or one or more other blood collection containers. In some embodiments, the third volume of blood may be collected in the third blood collection container 70c and/or one or more other blood collection containers.

In some embodiments, the distal end 50 of one or more of the first tubular instrument 48, the second tubular instrument 62, and the third tubular instrument 68 may include one or more side holes 72, which may facilitate blood flow into the catheter 14 proximal to the thrombus. In some embodiments, the distal end 50 of one or more of the first tubular instrument 48, the second tubular instrument 62, and the third tubular instrument 68 may be closed and/or may include a slit.

In some embodiments, the side holes 72 in the first tubular instrument 48 may be within the first distance or a particular distance the distal tip 16 extends beyond the catheter 14. In some embodiments, the side holes 72 in the second tubular instrument 62 may be within the second distance or a particular distance the distal tip 16 extends beyond the catheter 14. In some embodiments, the side holes 72 in the third tubular instrument 68 may be within the second distance or a particular distance the distal tip 16 extends beyond the catheter 14.

In some embodiments, one or more of the first tubular instrument 48, the second tubular instrument 62, and the third tubular instrument 68 may be resistant to occlusion and thrombosis because the slit may be closed, and blood may not be allowed to diffuse into the corresponding tubular instrument under normal physiological pressures. In some embodiments, the distal end 50 may include a distal opening.

In some embodiments, the difference between the first distance and the second distance and the difference between the second distance and the third distance may increase a likelihood of extension through the thrombus and establishment of the fluid pathway through the catheter assembly 20. In some embodiments, one or more particular delivery devices in addition to the first delivery device 44, the second delivery device 58, and the third delivery device 64 may be coupled to the catheter assembly 20 without removing the catheter 14 from the patient. In some embodiments, particular tubular instruments that are inserted through the dwelling catheter 14 as time progresses may be increasingly longer, which may increase a likelihood of establishing the fluid pathway through the catheter assembly 20 to allow blood draw and/or may reduce thrombosis.

In some embodiments, the first delivery device 44 may include a first marking 74a, which may be disposed on an outer surface of the first housing 46. In some embodiments, the second delivery device may include a second marking 74b, which may be disposed on an outer surface of the second housing 60. In some embodiments, the third delivery device 64 may include a third marking 74c, which may be disposed on an outer surface of the third housing 66. In some embodiments, the first marking 74a, the second marking 74b, and the third marking 74c may include one or more of a line, indent, groove, text, color, or another suitable marking.

In some embodiments, one or more of the first marking 74a, the second marking 74b, and the third marking 74c may include a time to use the corresponding delivery device. For example, the first marking 74a may include "Day 1" or "First Blood Draw." As another example, the second marking 74b may include "Day 2" or "Second Blood Draw." As a further example, the third marking 74c may include "Day 3" or "Third Blood Draw." In some embodiments, the first marking 74a, the second marking 74b, and/or the third marking 74c may indicate a time to use the corresponding delivery devices with respect to each other.

In some embodiments, the first housing 46 may include another marking 76a. In some embodiments, the first delivery device 44 may include the slider 41, which may be coupled to the first tubular instrument 48. In some embodiments, the slider 41 may be aligned with the other marking 76a in response to the distal surface 56 of the first tubular instrument 48 being flush with the distal tip 16 of the catheter 14. Thus, in some embodiments, the other marking 76a may indicate to the clinician that in response to further advancement of first tubular instrument 48 in a distal direction, the first tubular instrument 48 will extend distal to the distal tip 16 of the catheter 14.

In some embodiments, the second housing 60 may include the other marking 76b. In some embodiments, the second delivery device 58 may include the slider 41 that may be coupled to the second tubular instrument 62. In some embodiments, the slider 41 may be aligned with the other marking 76b in response to the distal surface 56 of the second tubular instrument 62 being flush with the distal tip 16 of the catheter 14. Similarly, in some embodiments, the third delivery device 64 may include the other marking 76c. In some embodiments, the third delivery device may include the slider 41, which may be coupled to the third tubular instrument 68. In some embodiments, the slider 41 may be aligned with the other marking 76c in response to the distal surface 56 of the third tubular instrument 68 being flush with the distal tip 16 of the catheter 14.

In some embodiments, the third housing 66 may be longer than the second housing 60, which may be longer than the first housing 46. Thus, the third tubular instrument 68, which may be longer than the second tubular instrument 62 and the first tubular instrument 48 may be contained within the third housing 66 prior to advancement in the distal direction. Similarly, in some embodiments, the second tubular instrument 62 may be contained within the second housing 60 prior to advancement in the distal direction, and the first tubular instrument 48 may be contained within the first housing 46 prior to advancement in the distal direction.

Referring now to FIG. 4, in some embodiments, a delivery device 80 may include a housing 82 and a tubular instrument 84. In some embodiments, the housing 82 may include one or more of the following: a first marking 86, a second marking 88, a third marking 90, and the slot 45. In some embodiments, the first marking 86, the second marking 88, and the third marking 90 may include one or more of a line, indent, groove, text, color, or another suitable marking.

In some embodiments, the first marking 86 may be proximal to the second marking 88. In some embodiments, the delivery device 80 may include the tubular instrument 84, which may include the distal end 50, the proximal end 43, and the lumen. In some embodiments, the proximal end of the tubular instrument may be secured within the housing 82. In some embodiments, the slider 41 may be coupled to the tubular instrument 84 and slidable along the slot 45 of the housing 82. In some embodiments, the slider 41 may include an advancement tab, which may be gripped by a clinician to advance and/or retract the tubular instrument.

In some embodiments, in response to advancing the slider 41 distally from a proximal position to the first marking 86, the distal surface 56 of the distal end 50 of the tubular instrument 84 may be disposed at a first distance beyond the distal end 32 of the housing 82 or the first distance beyond the distal tip 16 of the catheter 14. In some embodiments, in response to advancing the slider 41 distally from the proximal position to the second marking 88, the distal surface 56 of the distal end 50 of the tubular instrument may be disposed at a second distance beyond the distal end of the housing or the second distance beyond the distal tip 16 of the catheter 14.

In some embodiments, the second distance beyond the distal end 50 of the housing 82 may be greater than the first distance beyond the distal end 32 of the housing 82. As mentioned previously, in some embodiments, the second distance beyond the distal tip 16 of the catheter 14 may be greater than the first distance beyond the distal tip 16 of the catheter 14.

In some embodiments, in response to advancing the slider 41 distally from the proximal position to the third marking 90, the distal surface 56 of the distal end of the tubular instrument 84 may be disposed at a third distance beyond the distal end 32 of the housing 82. In some embodiments, the third distance may be greater than the second distance. In some embodiments, the third distance beyond the distal end 32 of the housing 82 may be greater than the second distance beyond the distal end 32 of the housing 82. As mentioned previously, in some embodiments, the third distance beyond the distal tip 16 of the catheter 14 may be greater than the second distance beyond the distal tip 16 of the catheter 14.

In some embodiments, different blood collection containers or a same blood collection container may be used to collect blood via the delivery device 80 or any of the other delivery devices of the present disclosure. In some embodiments, the slider 41 may be advanced distally from the proximal position to the first marking 86 at a first duration of time for a first blood draw. In some embodiments, the slider 41 may be advanced distally from the first marking 86 to the second marking 88 at a second duration of time later than the first duration of time. In some embodiments, the slider 41 may be advanced distally from the second marking 88 to the third marking 90 at a third duration of time later than the second duration of time. In some embodiments, the first duration of time may correspond to about one day. In some embodiments, the second duration of time and the third duration of time may correspond to about two days and about three days, respectively. In some embodiments, the first duration of time, the second duration of time, and the third duration of time may correspond to any suitable duration of time from insertion of the catheter 14 into the vasculature.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

We claim:

1. A method, comprising:
   coupling a first delivery device to a catheter assembly, wherein the catheter assembly comprises a catheter dwelling within vasculature of a patient, wherein the first delivery device comprises:
   a first housing; and
   a first tubular instrument, comprising a distal end, a proximal end, and a lumen extending between the distal end of the first tubular instrument and the proximal end of the first tubular instrument, wherein the proximal end of the first tubular instrument is secured within the first housing, wherein the first tubular instrument is configured to advance distally from a proximal position to a distal position with respect to the first housing and the catheter assembly, wherein in response to the first tubular instrument being in the proximal position, the first tubular instrument is proximal to the catheter assembly, wherein in response to the first tubular instrument being in the distal position, a distal surface of the first tubular instrument is disposed distal to a distal tip of a catheter of the catheter assembly and at a first distance beyond the distal tip of the catheter;
   after transferring a first volume of blood via the first tubular instrument to a first blood collection container and moving the first tubular instrument from the distal position toward the proximal position, decoupling the first delivery device from the catheter assembly;
   after decoupling the first delivery device from the catheter assembly, coupling a second delivery device to the catheter assembly, wherein the second delivery device comprises:
   a second housing;
   a second tubular instrument, comprising a distal end, a proximal end, and a lumen extending between the distal end of the second tubular instrument and the proximal end of the second tubular instrument, wherein the proximal end of the second tubular instrument is secured within the second housing, wherein the second tubular instrument is configured to advance distally from another proximal position to another distal position with respect to the second housing and the catheter, wherein in response to the second tubular instrument being in the proximal position, the second tubular instrument is proximal to the catheter assembly, wherein in response to the second tubular instrument being in the distal position, a distal surface of the second tubular instrument is disposed distal to the distal tip of the catheter and at a second distance from the distal tip of the catheter, wherein the second distance is greater than the first distance; and
   after transferring a second volume of blood via the second tubular instrument to a second blood collection container and moving the second tubular instrument from the distal position toward the proximal position, decoupling the second delivery device from the catheter assembly.

2. The method of claim 1, wherein a difference between the first distance and the second distance is 0.5 inches.

3. The method of claim 1, wherein the first distance is 1 inch or less.

4. The method of claim 3, wherein the second distance is 1.5 inches or less.

5. The method of claim 1, further comprising transferring the first volume of blood via the first tubular instrument to the first blood collection container on a first day, further comprising transferring the second volume of blood via the second tubular instrument to the second blood collection container on a second day.

6. The method of claim 1, wherein the distal end of the first tubular instrument and the distal end of the second tubular instrument are closed.

7. The method of claim 1, wherein the distal end of the first tubular instrument and the distal end of the second tubular instrument comprise a plurality of side holes.

8. The method of claim 1, further comprising:
coupling a third delivery device to the catheter assembly, wherein the third delivery device comprises:
a third housing; and
a third tubular instrument, comprising a distal end, a proximal end, and a lumen extending between the distal end of the third tubular instrument and the proximal end of the third tubular instrument, wherein the proximal end of the third tubular instrument is secured within the third housing, wherein the third tubular instrument is configured to advance distally from another proximal position to another distal position with respect to the third housing and the catheter, wherein in response to the third tubular instrument being in the other proximal position, the third tubular instrument is proximal to the catheter assembly, wherein in response to the third tubular instrument being in the other distal position, a distal surface of the third tubular instrument is disposed distal to the distal tip of the catheter and at a third distance from the distal tip of the catheter, wherein the third distance is greater than the second distance.

9. The method of claim 8, wherein the third distance is 2.0 inches or less.

10. The method of claim 9, wherein a difference between the second distance and the third distance is 0.5 inches.

11. A blood draw kit, comprising:
a first delivery device, comprising:
a first housing, wherein a distal end of the first housing comprises a first adapter configured to couple to a catheter assembly; and
a first tubular instrument, comprising a distal end, a proximal end, and a lumen extending between the distal end of the first tubular instrument and the proximal end of the first tubular instrument, wherein the proximal end of the first tubular instrument is secured within the first housing, wherein the first tubular instrument is configured to advance distally from a proximal position to a distal position with respect to the first housing and the catheter assembly, wherein in response to the first tubular instrument advancing distally from the proximal position to the distal position with respect to the first housing, a distal surface of the distal end of the first tubular instrument is disposed at a first distance beyond the distal end of the first housing;
a second delivery device, comprising:
a second housing, wherein a distal end of the second housing comprises a second adapter configured to couple to the catheter assembly; and
a second tubular instrument, comprising a distal end, a proximal end, and a lumen extending between the distal end of the second tubular instrument and the proximal end of the second tubular instrument, wherein the proximal end of the second tubular instrument is secured within the second housing, wherein the second tubular instrument is configured to advance distally from a proximal position to a distal position with respect to the second housing and the catheter assembly, wherein in response to the second tubular instrument advancing distally from the proximal position to the distal position with respect to the second housing, a distal surface of the distal end of the second tubular instrument is disposed at a second distance beyond the distal end of the second housing, wherein the second distance is greater than the first distance.

12. The blood draw kit of claim 11, wherein the distal end of the first tubular instrument and the distal end of the second tubular instrument are closed.

13. The blood draw kit of claim 11, wherein the distal end of the first tubular instrument and the distal end of the second tubular instrument comprise a plurality of side holes.

14. The blood draw kit of claim 11, further comprising:
a third delivery device, comprising:
a third housing, wherein a distal end of the third housing comprises a third adapter configured to couple to the catheter assembly; and
a third tubular instrument, comprising a distal end, a proximal end, and a lumen extending between the distal end of the third tubular instrument and the proximal end of the third tubular instrument, wherein the proximal end of the third tubular instrument is secured within the third housing, wherein the third tubular instrument is configured to advance distally from a proximal position to a distal position with respect to the third housing and the catheter assembly, wherein in response to the third tubular instrument advancing distally from the proximal position to the distal position with respect to the third housing, a distal surface of the distal end of the third tubular instrument is disposed at a third distance beyond the distal end of the third housing, wherein the third distance is greater than the second distance.

15. The blood draw kit of claim 14, wherein the third housing is longer than the second housing, and wherein the second housing is longer than the first housing.

16. The blood draw kit of claim 14, wherein the third tubular instrument is longer than the second tubular instrument, and wherein the second tubular instrument is longer than the first tubular instrument.

17. The blood draw kit of claim 11, wherein the first housing comprises a first marking representative of a first time of use for the first delivery device, and the second housing comprises a second marking representative of a second time of use for the second delivery device.

18. The blood draw kit of claim 17, wherein the first housing comprises a second marking and a slot, wherein the first delivery device further comprises a slider coupled to the first tubular instrument and slidable along the slot, and wherein in response to advancing the slider to the second marking, a distal surface of the distal end of the first tubular instrument is flush with a distal tip of the catheter assembly.

19. The blood draw kit of claim 11, wherein the second housing is longer than the first housing.

20. The blood draw kit of claim 11, wherein the second tubular instrument is longer than the first tubular instrument.

* * * * *